(12) United States Patent
Shuey et al.

(10) Patent No.: US 7,402,713 B2
(45) Date of Patent: Jul. 22, 2008

(54) PROCESSES FOR CONVERSION OF TYROSINE TO P-HYDROXYSTYRENE AND P-ACETOXYSTYRENE

(75) Inventors: Steven W. Shuey, Landenberg, PA (US); Mukesh C. Shah, Hockessin, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 168 days.

(21) Appl. No.: 11/369,422

(22) Filed: Mar. 7, 2006

(65) Prior Publication Data

US 2007/0213569 A1  Sep. 13, 2007

(51) Int. Cl.
*C07C 37/00* (2006.01)
*C07C 69/84* (2006.01)
*C07C 65/03* (2006.01)

(52) U.S. Cl. .................. 568/766; 560/130; 562/478

(58) Field of Classification Search .................. None
See application file for complete search history.

(56) References Cited

U.S. PATENT DOCUMENTS

| | | | |
|---|---|---|---|
| 4,316,995 A | 2/1982 | Pittet et al. | |
| 5,274,060 A | 12/1993 | Schadeli | |
| 5,324,804 A | 6/1994 | Steinmann | |
| 5,493,062 A | 2/1996 | Sounik et al. | |
| 7,009,057 B2 * | 3/2006 | Halama et al. | 546/269.7 |
| 2004/0248267 A1 | 12/2004 | Ben-Bassat et al. | |
| 2005/0228291 A1 | 10/2005 | Chance | |

FOREIGN PATENT DOCUMENTS

| | | |
|---|---|---|
| AU | 47129 | 4/1974 |
| WO | WO 02088120 | * 11/2002 |

OTHER PUBLICATIONS

Richard C. Sovish, Preparation and Polymerization of P-Vinylphenol, J. Org. Chem., 1959, vol. 24:1345-1347.
D. Munteanu et. al., Synthesis of the Monomeric Antioxidant, Journal of Thermal Anal., 1991, vol. 37:411-426.
Carol J. Simpson et. al., Preparation of Vinylphenols From 2-and 4-Hydroxybenzaldehydes, Tetrahedron Letters, 2005, vol. 46:6893-6896.
Z. Naturforsch et. al., Synthesis and Characterization of a Novel Ferroelectric Liquid Crystal Compound Derived From L-Tyrosine, 2002, 57A:803-806.
Andrew J. Souers et. al., Al., Preparation of Enantioenriched A-Bromo Acids Incorporating Diverse Functionality, Synthesis, 1999, vol. 4:583-585.
Abstract, Bernard, T. et al., Phytochemistry Beilstein Registry No. 6720706, 1981, p. 2325-2326, vol. 20, No. 10, Beilstein Institute for Organic Chemistry.
Abstract, Merling, Justus Liebigs Ann. Chem., Beilstein Registry No. 7915986, 1981, p. 19, vol. 209, Beilstein Institute for Organic Chemistry.

* cited by examiner

*Primary Examiner*—Rosalynd Keys

(57) ABSTRACT

Tyrosine was converted to p-hydroxystyrene in a two-step reaction without purification of individual intermediates. Conditions were determined for bromination of tyrosine in which reactive intermediates were formed. The mixture of these intermediates was used directly in a second step reaction to produce p-hydroxystyrene. The p-hydroxystyrene was further acetylated to produce p-acetoxystyrene in the second step reaction vessel.

23 Claims, No Drawings

PROCESSES FOR CONVERSION OF TYROSINE TO P-HYDROXYSTYRENE AND P-ACETOXYSTYRENE

FIELD OF INVENTION

The invention relates to the field of organic synthesis. More specifically, the invention relates to a method for preparing p-hydroxystyrene monomers from tyrosine by diazobromination and elimination/decarboxylation in a two-step reaction. In an additional reaction p-acetoxystyrene is prepared.

BACKGROUND OF THE INVENTION

Hydroxystyrenes, such as p-hydroxystyrene (pHS; also known as p-vinylphenol) and acetylated derivatives thereof, such as p-acetoxystyrene (pAS), are aromatic compounds that have potential utility in a wide variety of industrial applications. For example, these compounds have applications as monomers for the production of resins, elastomers, adhesives, coatings, automotive finishes, inks and photoresists, as well as in electronic materials. They may also be used as additives in elastomer and resin formulations.

A number of methods for the chemical synthesis of hydroxystyrenes and acetylated derivatives thereof are known. However, these methods generally require expensive reagents, harsh conditions, and give relatively low yields. Examples of starting reagents used in the chemical synthesis of pHS include p-hydroxycinnamic acid (pHCA; Sovish *J. Org. Chem.* 24:1345-1347 (1959); U.S. Pat. No. 5,274,060), p-hydroxybenzaldehyde (U.S. Pat. No. 4,316,995), ortho or para-hydroxyarylcarboxylic acids (Australian Patent Application No. 7247129), caffeic acid (U.S. Pat. No. 5,324,804), trans-3,5-di-tert-butyl-4-hydroxycinnamic acid (Munteanu et al. *J. Thermal Anal.* 37:411-426 (1991)), and p-alpha-amino-ethylphenol (U.S. Pat. No. 5,493,062), and hydroxybenzaldehydes and malonic acid (Simpson et al., Tetraheron Lett. 46: 6893 (2005)).

Tyrosine, (S)-2-amino-3-(4-hydroxy-phenyl)propanoic acid, provides a readily available and relatively low cost reagent which has potential of being a reagent for producing pHS. Tyrosine was used as the starting reagent in the synthesis of (S)4-(2-chloro-3-(4-n-dodecyloxy)phenylpropionato)-4'4(2-methyl)butyloxy-biphenylcarboxylate (CDPMBB) in Kumar and Pisipati (Z. Naturforsch. 57a:803-806 (2002)). The initial reaction was diazochlorination of tyrosine by nucleophilic substitution in the presence of sodium nitrite to form (S)-2-chloro-3-(4-hydroxy)phenyl propionic acid. Yields of the reaction were poor, and by-products resulting from nitration or chlorination of the aromatic ring made purification difficult.

Side chain protected tyrosine, tyrosine t-butyl ether, was brominated in the presence of HBr, KBr, and sodium nitrite (Souers et al., Synthesis 4:583-585 (1999)). The presence of the protecting group on the phenol moiety complicates the use of this product as a reagent for producing pHS.

There is a need for a method for the chemical synthesis of pHS from tyrosine which is simple and efficient, that produces product in high yield and avoids the complications of by products generated from the use of a side chain protected tyrosine. Applicants have solved the stated problem by the discovery of a two step reaction for the conversion of tyrosine to brominated tyrosine intermediates coupled with their subsequent conversion to p-hydroxstyrene under basic conditions.

SUMMARY OF THE INVENTION

Methods are provided for the synthesis of p-hydroxystyrene. The method proceeds with the reaction of tyrosine in the presence of HBr and NaNO2 to form an isomeric mixture of brominated tyrosine intermediates which are subsequently converted to p-hydroxystyrene in the presence of a base catalyst. Additionally, p-hydroxystyrene produced by this method may be converted directly or after isolation to p-acetoxystyrene in the presence of an acetylating agent.

Accordingly, in one embodiment the invention provides a method for the synthesis of p-hydroxystyrene comprising:

a) reacting tyrosine in the presence of HBr and NaNO2 to form an isomeric mixture of 2-bromo-(3-p-hydroxyphenyl) propionic acid and 3-bromo-(2-p-hydroxyphenyl) propionic acid, according to Formula I:

Formula I:

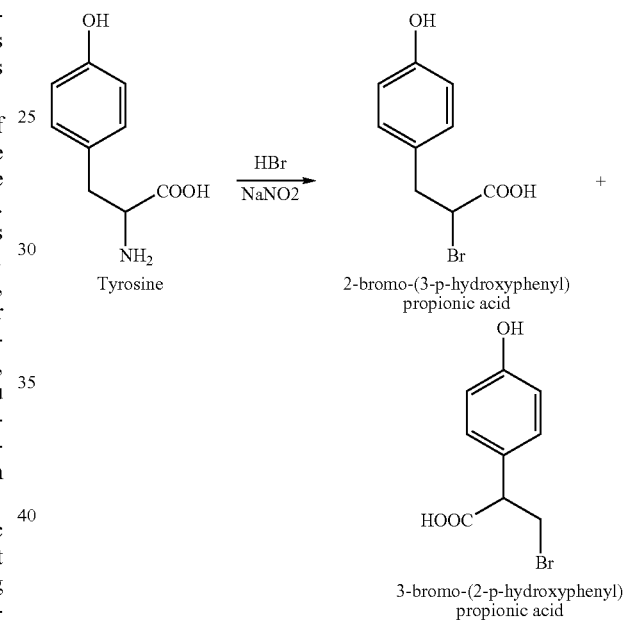

b) isolating the isomeric product of (a); and c) reacting the isolated isomeric product of b) with a basic catalyst in an organic solvent wherein p-hydroxystrene is produced according to Formula II Formula II:

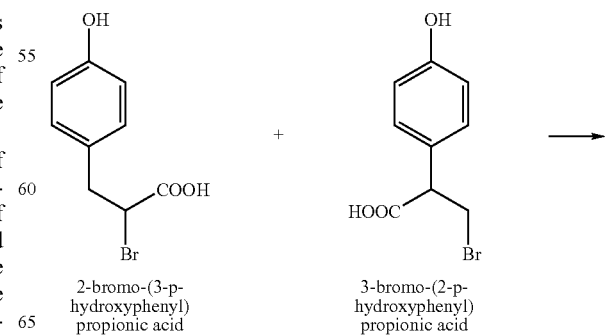

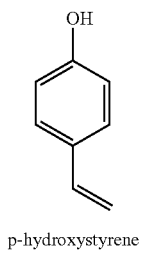

p-hydroxystyrene

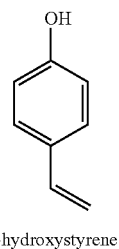

p-hydroxystyrene

Similarly in an alternate embodiment the invention provides a method for the synthesis of p-acetoxystyrene comprising:

a) reacting tyrosine in the presence of HBr and NaNO2 to form an isomeric mixture of 2-bromo-(3-p-hydroxyphenyl) propionic acid and 3-bromo-(2-p-hydroxyphenyl) propionic acid, according to Formula I:

Formula I:

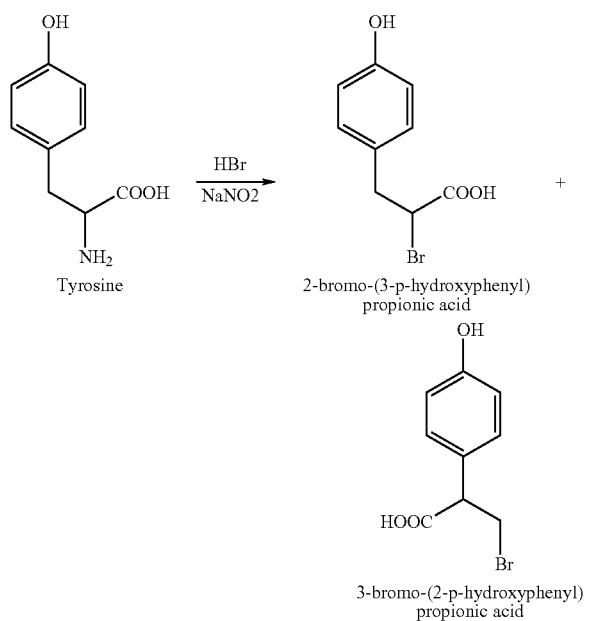

b) isolating the isomeric product of (a); and
c) reacting the isolated isomeric product of b) with a basic catalyst in an organic solvent wherein p-hydroxystrene is produced according to Formula II Formula II:

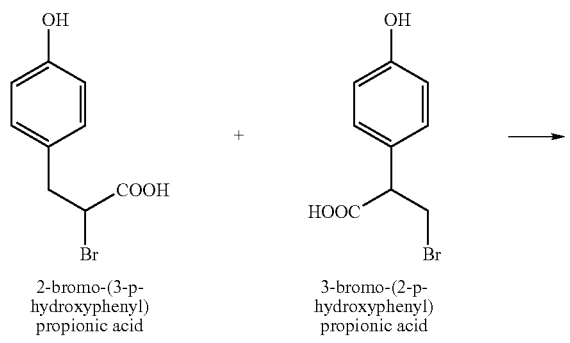

and d) reacting the p-hydroxystyrene of step (c) with an acetylating agent wherein p-acetoxystyrene is formed.

In another embodiment the invention provides compositions having the general formulae:

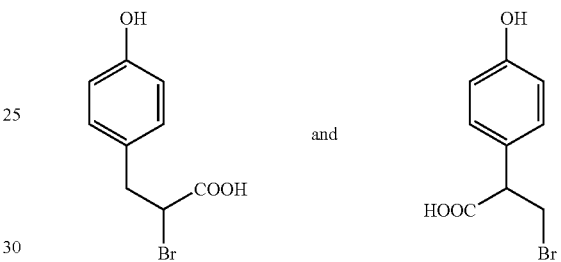

DETAILED DESCRIPTION OF THE INVENTION

The invention provides a two-step process for preparing p-hydroxystyrene from tyrosine. The first step involves the diazobromination of tyrosine, followed by a 2-stage sequence of elimination of bromide and base catalyzed, thermal decarboxylation. Additionally the invention contemplates conversion of the p-hydroxystyrene in the presence of an acetylating agent to p-acetoxystyrene.

Both p-hydroxystyrene and p-acetoxystyrene find utility as monomers for use in commercial resins, elastomers, adhesives, coatings, automotive finishes, inks, photoresists, electronic materials, and additives in elastomer and resin formulations.

The following definitions are used herein and should be referred to for interpretation of the claims and the specification.

"p" means para.

"pAS" is the abbreviation used for para-acetoxystyrene which is also represented as p-acetoxystyrene or 4-acetoxystyrene.

"pHS" is the abbreviation used for para-hydroxystyrene which is also represented as p-hydroxystyrene or 4-hydroxystyrene.

The term "yield" as used herein refers to the amount of product produced in a chemical reaction. The yield is typically expressed as a percentage of the theoretical yield for the reaction. The term "theoretical yield" means the predicted amount of product to be expected based on the amount of substrate initially present and the stoichiometry of the reaction.

The term "polar" as applied to solvents of the invention refers to solvents characterized by molecules having sizable permanent dipole moments.

The term "aprotic" as applied to the solvents of the invention refers to a solvent that is incapable of acting as a labile proton donor or acceptor.

The term "protic" as applied to the solvents of the invention refers to a solvent that is capable of acting as a labile proton donor or acceptor.

The term "polar organic solvent mixture" refers to a mixture of organic solvents comprising at least one polar solvent.

The term "aprotic, polar organic solvent mixture" refers to a mixture of organic solvents comprising at least one aprotic, polar solvent.

The term "complete" as it is used relative to the term of a chemical reaction refers to the point where the maximum product has been formed under the conditions of the reaction.

The term "brominated tyrosine intermediates" refers principally to the compounds 2-bromo-(3-p-hydroxyphenyl) propionic acid and 3-bromo-(2-p-hydroxyphenyl) propionic acid.

All ranges given herein include the end of the ranges and also all the intermediate range points.

In one embodiment the invention provides a process for the production of pHS from unprotected tyrosine in a two step process. The process involves the generation of brominated tyrosine intermediates which may be isolated as a mixture, and then reacted with a basic catalyst for the production of PHS in good yield.

First Stage Reaction

The first step of the reaction proceeds according to the following scheme:

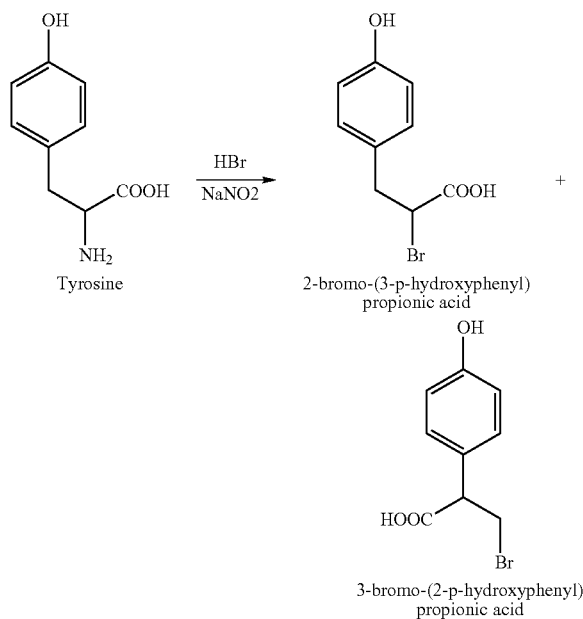

Unprotected tyrosine is reacted in the presence of HBr and NaNO2 for the production of brominated tyrosine intermediates (2-bromo-(3-p-hydroxyphenyl) propionic acid and 3-bromo-(2-p-hydroxyphenyl) propionic acid) and other minor brominated tyrosine intermediates. These products are referred to herein as an isomeric bromide product mixture.

Tyrosine substrate may be derived from any source. Tyrosine may be chemically synthesized or biologically produced, such as through fermentation as described in US 20050148054A1, herein incorporated by reference. Tyrosine is commercially available, for example, from Aldrich (Milwaukee, Wis.). D-tyrosine, L-tyrosine, or a mixture of D- and L-tyrosine may be used.

In addition to hydrobromic acid (HBr), and sodium nitrite ($NaNO_2$) the reaction may optionally contain a bromide salt such as potassium bromide (KBr) or sodium bromide (NaBr).

The reaction may be run under a nitrogen blanket, however the absence of oxygen is not necessary.

Typically HBr in the reaction mixture is in a final concentration that is between about 0.5 M and about 6.0 M. More suitable is a final concentration of HBr that is between about 0.6 M and about 2.5 M. Particularly suitable is an HBr concentration between about 0.75 M and about 1.5 M. The use of bromine free HBr is preferred to avoid bromination of the phenolic ring. HBr may be purchased in bromine free form. If an HBr reagent is not bromine free, the HBr may be purified prior to addition to the reaction mixture by methods well known to one skilled in the art, examples of which are found in "Purification of Laboratory Chemicals $3^{rd}$ Edition" D. D. Perrin & W. L. F Armarego, Pergamon Press (1988). For example, an HBr reagent solution may be washed with 5% tributylphosphate in chloroform to remove free bromine.

$NaNO_2$ is also commercially available and is typically present in the reaction at a concentration of about 1 mole equivalent to about 3 mole equivalents as compared to the substrate tyrosine. The concentration of $NaNO_2$ will also be varied depending on the concentration of the other reactants as is commonly known to those of skill in this art.

Where used, the bromide salt, will be present in the reaction mixture at a concentration that will maintain the solubility of the salt under the conditions used. Solubility will be affected both by the concentration of tyrosine, HBr and $NaNO_2$, and the temperature and pressure under which the reaction is run. Typically the mole equivalent of the bromide salt in the reaction is less than about 4.

Reactions proceed at temperatures of about −10° C. and about 25° C., and preferably between about −5° C. and about 10° C.

The order of adding the reactants is not critical. Typically, a mixture of HBr and NaBr or KBr is chilled to the reaction temperature and then combined with tyrosine. Generally it is preferred if the tyrosine becomes soluble in the reaction. An alternate order of addition to that stated above is, for example, first cooling an HBr solution, then adding KBr and stirring to form a solution, then adding $NaNO_2$, and finally adding tyrosine over time while maintaining the cooled temperature.

As is typical of reactions of this sort, the yields of brominated tyrosine intermediates will vary depending on the relative concentration of reactants and the temperature and pressure of the reaction. One of skill in the art will readily be able to determine the preferred concentration of reactants for maximum yield of production. Some non-limiting variations are illustrated in Table 3 of the Examples.

Reagent concentrations tested that gave the highest yields include: 1) 2 equivalents of $NaNO_2$, 0.75 M HBr, and 2 equivalents of KBr; and 2) 1 equivalent of $NaNO_2$, 2.375 M HBr, and 2 equivalents of KBr. The optimal reaction predicted from a model (Design of Experiments (DOE) analysis using Minitab™) derived from the data of Table 3, providing a particularly suitable set of reagent concentrations, includes 1 equivalent of $NaNO_2$, 0.75 M HBr, and 2 equivalents of KBr.

The reaction times will vary depending on conditions and reactant concentrations however most reactions will be complete in less than four hours and reaction times of about 45 minutes to about 120 minutes are typical. Monitoring for completion of the reaction is known to one skilled in the art, and can be performed using a method such as HPLC analysis, for example.

After completion of the reaction the isomeric bromide product mixture may be isolated using any suitable method known in the art, such as extraction, crystallization and chromatography. Specifically, the product mixture may be extracted with an organic solvent, the organic layers washed with brine and dried, and the solvent removed by rotary evaporation. The product mixture may be further purified by silica gel chromatography with further organic extraction, brine washes, drying, and solvent removal.

Isolation of the individual brominated tyrosine intermediates (2-bromo-(3-p-hydroxyphenyl) propionic acid and 3-bromo-(2-p-hydroxyphenyl) propionic acid) from each other is not required in the present process. However, these two compounds may be individually isolated by methods well known in the art such as column chromatography or crystallization, Specifically, the individual compounds may be isolated using reverse phase chromatography on a preparative HPLC column as described in Example 10.

Second Stage Reaction

The isolated isomeric bromide product mixture is reacted to eliminate Br and is decarboxylated as shown below. There is no need to isolate individual products of the isomeric mixture prior to the second step reaction.

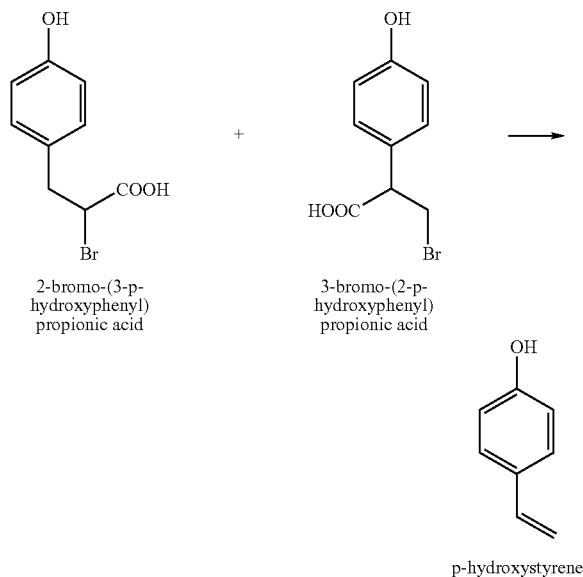

The second stage reaction proceeds in the presence of a basic catalyst provided in an organic solvent where the reaction may optionally be run under a nitrogen blanket. Optionally a polymerization inhibitor or retarder may be added.

A wide variety of organic solvents may be used, including both aprotic polar organic solvents and protic polar organic solvents. A single protic, polar organic solvent or a single aprotic, polar organic solvent may be used. Additionally, mixtures of aprotic, polar solvents, mixtures of protic, polar solvents, mixtures of aprotic and protic, polar solvents, and mixtures of aprotic or protic solvents with nonpolar solvents may be used, wherein aprotic, polar solvents or mixtures thereof are more suitable. Suitable aprotic polar organic solvents include, but are not limited to, N,N-dimethylformamide, 1-methyl-2-pyrrolidinone, N,N-dimethylacetamide, dimethylsulfoxide, hexamethylphosphoramide, and hexamethylphosphorous triamide. Particularly suitable aprotic, polar organic solvents are N,N-dimethylformamide and N,N-dimethylacetamide. Suitable protic, polar solvents include, but are not limited to, di(propylene glycol) methyl ether (Dowanol™ DPM), di(ethylene glycol) methyl ether, 2-butoxyethanol, ethylene glycol, 2-methoxyethanol, propylene glycol methyl ether, n-hexanol, and n-butanol.

The basic catalyst may be any basic catalyst that is capable of facilitating the present reactions. Such catalysts include, but are not limited to, potassium acetate, potassium carbonate, potassium hydroxide, sodium acetate, sodium carbonate, sodium bicarbonate, sodium hydroxide, magnesium oxide, pyridine and triethylamine. Weakly basic catalysts are more suitable, including potassium carbonate, sodium carbonate, sodium hydroxide, triethylamine, and potassium acetate. Particularly suitable are potassium carbonate and sodium carbonate. Basic catalysts suitable in the present invention are available commercially from, for example, EM Science (Gibbstown, N.J.) or Aldrich (Milwaukee, Wis.).

The optimum concentration of basic catalyst will vary depending on the concentration of substrate, nature of the solvent used and reaction conditions. Typically, concentrations of about 1 mol % to about 30 mol % relative to the substrate, are used in the reaction mixture.

Typically the reaction will be run at a temperature of is between about 50° C. and about 150° C. Optionally the temperature of the reaction may be achieved in a stepwise manner.

Reaction times to completion will vary however, most reactions will run to completion in less than four hours and reaction times of about 45 minutes to about 20 hours are typical.

Polymerization Inhibitors

Polymerization inhibitors are useful but not required in the methods of the invention. Any suitable polymerization inhibitor that is tolerant of the temperatures required for the decarboxylation (second step) reaction as described in the invention may be used. Examples of suitable polymerization inhibitors include, but are not limited to, hydroquinone, hydroquinone monomethylether, 4-tert-butyl catechol, phenothiazine, N-oxyl (nitroxide) inhibitors, including Prostabe® 5415 (bis(1-oxyl-2,2,6,6-tetramethylpiperidine-4-yl)sebacate, CAS#2516-92-9, available from Ciba Specialty Chemicals, Tarrytown, N.Y.), 4-hydroxy-TEMPO (4-hydroxy-2,2, 6,6-tetramethylpiperidin-1-yloxy, CAS#2226-96-2, available from TCI America) and Uvinul® 4040 P (1,6-hexamethylene-bis(N-formyl-N-(1-oxyl-2,2,6,6-tetramethylpiperidine-4-yl)amine available from BASF Corp., Worcester, Mass.).

Polymerization Retarders

In some instances it may be advantageous to use a polymerization retarder in the present reaction in combination with the polymerization inhibitor. Polymerization retarders are well known in the art and are compounds that slow down the polymerization reaction but cannot prevent it altogether. Common retarders are aromatic nitro compounds such as dinitro-ortho-cresol (DNOC) and dinitrobutylphenol (DNBP). Methods for the preparation of polymerization retarders are common and well known in the art (see for example U.S. Pat. No. 6,339,177; Park et al., *Polymer* (Korea) (1988), 12(8), 710-19) and their use in the control of styrene polymerization is well documented (see for example Bushby et al., *Polymer* (1998), 39(22), 5567-5571).

Acetylation of p-Hydroxystyrene

In another embodiment of the invention p-hydroxystyrene may be acetylated to pAS as shown below:

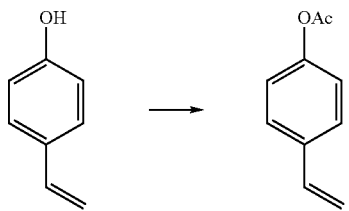

The p-hydroxystyrene product may be transferred from the second stage reaction to another vessel for acetylation, or the p-hydroxystyrene product may be converted to an acetylated derivative by adding an acetylating agent directly to the reaction mixture after completion of the decarboxylation reaction.

For a combined decarboxylation-acetylation process, organic solvents used should have the net characteristics of being both aprotic and polar. A single aprotic, polar solvent may be used, or a mixture of aprotic, polar solvents may be used. Alternatively, an aprotic, polar solvent may be used in combination with a non-polar solvent; however, protic solvents are undesirable because they tend to consume acetylating agent due to their reactivity. Solvents suitable in the decarboxylation-acetylation process of the invention include, but are not limited to, N,N-dimethylformamide, 1-methyl-2-pyrrolidinone, N,N-dimethylacetamide, dimethylsulfoxide, hexamethylphosphoramide, and hexamethylphosphorous triamide. Particularly suitable solvents are N,N-dimethylformamide and N,N-dimethylacetamide.

Typically the acetylating agent is used in excess where a concentration of at least 1 mole equivalent as compared to the substrate is particularly suitable. Suitable acetylating agents include, but are not limited to, acetic anhydride and acetyl chloride.

The acetylation reaction may be carried out with high yield at temperatures ranging from about 0° C. to about 150° C., and more suitably at temperatures ranging from about 50° C. to about 140° C. One skilled in the art will recognize that a temperature at which both the substrate and the catalyst are soluble is preferred. The simplest approach is to add the acetylating agent just after completion of the decarboxylation reaction step and to perform the acetylation at the same temperature as the decarboxylation reaction. In one embodiment this is accomplished using DMF (N,N-dimethylformamide) and potassium carbonate in elimination and decarboxylation at 65° C., then adding acetic anhydride for acetylation at the same temperature.

Isolation and Purification of p-Hydroxystrene and p-Acetoxystyrene Products

The p-hydroxystyrene product or the p-acetoxystyrene product may be isolated using any suitable method known in the art. For example, the solvent may be removed by reduced pressure distillation. The p-hydroxystyrene product or the acetylated derivative thereof may be further purified using vacuum distillation or chromatographic techniques that are well known in the art.

The resultant p-hydroxystyrene or p-acetoxystyrene may then be used as monomers for the production of, for example, resins, elastomers, adhesives, coatings, automotive finishes, inks, photoresists and as additives in elastomer and resin formulations.

EXAMPLES

The present invention is further defined in the following Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "sec" means second(s), "mL" means milliliter(s), "L" means liter(s), "μL" means microliter(s), "μm" means micrometer(s), "mol" means mole(s), "mmol" means millimole(s), "g" means gram(s), "mg" means milligram(s), "M" means molar concentration, "m" means molal concentration, "eq" means equivalents, "v/v" means volume to volume ratio, "Pa" means pascal, "mPa" means millipascal, "psig" means pounds per square inch gauge, "HPLC" means high performance liquid chromatography, "DMF" means N,N-dimethylformamide, "DMAc" means N,N-dimethylacetamide, "NMP" means 1-methyl-2-pyrrolidinone, and "kPa" means kilopascal(s).

General Methods:

Reagents:

All solvents were reagent grade and were obtained from Aldrich (Milwaukee, Wis.) unless noted otherwise. The basic catalysts used were obtained from Aldrich or EM Science (Gibbstown, N.J.).

HPLC Methods:

For measuring the Brominated Intermediates

Method 1: An Agilent 1100 HPLC system (Agilent Technologies, Wilmington, Del.) was used with a reverse-phase Zorbax SB-C18 column (4.6 mm×150 mm, 3.5 μm, supplied by Agilent Technologies. The HPLC separation was achieved using a gradient combining two solvents: Solvent A, 0.1% trifluoroacetic acid in HPLC grade water and Solvent B, 0.1% trifluoroacetic acid in acetonitrile. The mobile phase flow rate was 1.25 mL/min. The solvent gradient used is given in Table 1. A temperature of 40° C. and a sample injection of 5 μL were used.

TABLE 1

| Solvent Gradient Used for HPLC Method 1 | | |
|---|---|---|
| Time (min) | Solvent A | Solvent B |
| 0 | 90% | 10% |
| 30 | 43% | 57% |
| 35 | 20% | 80% |
| 40 | 90% | 10% |

After each run, the column was re-equilibrated for 5 min with a solvent mixture of 90% A and 10% B.

Suitable calibration curves were generated using standard solutions of the brominated products and tyrosine. The brominated products for the standards were prepared from using similar methods to Example 1 and purifying the two components by preparative HPLC. The brominated intermediates were assayed using quantitative NMR to determine purity. The calibration curves were used to determine wt % of brominated intermediates (compounds 1 and 2 in Diagram I) in each sample from HPLC peak areas. With this information and the total weight of the reaction mixture at the time of sampling, the % conversion of tyrosine and the % yield of brominated intermediates were calculated.

For measuring HSM from Step 2 Reaction

Method 2: The Agilent 1100 HPLC system was used with a reverse-phase Zorbax SB-C18 column (4.6 mm×150 mm, 3.5 µm, supplied by Agilent Technologies). The HPLC separation was achieved using a gradient combining two solvents: Solvent A, 0.1% trifluoroacetic acid in HPLC grade water and Solvent B, 0.1% trifluoroacetic acid in acetonitrile. The mobile phase flow rate was 1.0 mL/min. The solvent gradient used is given in Table 2. A temperature of 40° C. and a sample injection of 1 µL were used.

TABLE 2

Solvent Gradient Used for HPLC Method 2

| Time (min) | Solvent A | Solvent B |
|---|---|---|
| 0 | 95% | 5% |
| 10 | 100% | 0% |
| 12 | 100% | 0% |
| 12.5 | 95% | 5% |

Suitable calibration curves were generated as described above and used to determine wt % of pHS in each sample from HPLC peak areas. With this information and the total weight of the reaction mixture at each time point, the weight and moles of pHS versus time were calculated.

Example 1

First Step Reaction: Synthesis of 2-Bromo-(3-p-hydroxyphenyl) propionic acid and 3-Bromo-(2-p-hydroxyphenyl) propionic acid In the first step reaction an isomeric bromide product mixture was made from tyrosine, with the major reaction products being the two compounds shown below:

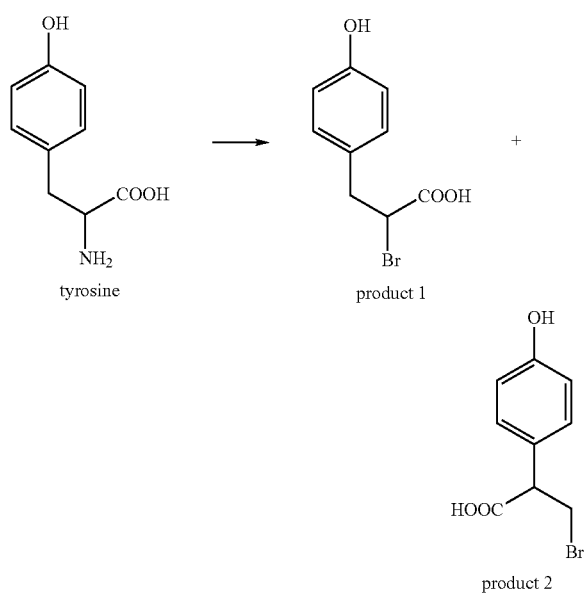

A first step reaction was performed as follows. Into a 1L 3-neck flask equipped with a thermometer, an overhead mechanical stirrer and an addition port was added under nitrogen 523.9 g of 1.5 M HBr. The HBr solution had been freshly washed with 5% tributylphosphate in chloroform to remove free bromine. The flask and contents were cooled to 5° C. and 12.78 g of NaBr was added in one portion, resulting in a clear solution. DL-Tyrosine (15 g) was added and the mixture stirred until a clear solution formed. Sodium nitrite, 7.426 g, was added portionwise over 30 min so that the temperature did not go above 10° C. The solution turned to light yellow with gas evolution and turned darker as the addition of $NaNO_2$ was complete. The mixture was allowed to stir at 5° C. for 1.5 h. Analysis by HPLC (as described in General Methods) showed the reaction to be complete with a yield of 74%. The cold solution was transferred to a 1 L separatory funnel and extracted 3× with 200 mL cold ether. The combined organic layers were washed with 30 mlL brine and then dried over sodium sulfate. Removal of the solvent by rotary evaporation gave 24.75 g of the crude product as a brown oil. The crude product was dissolved in ether/EtOAc (4 parts to 1 part by volume) and chromatographed on silica gel eluting with 4:1 ether:EtOAc containing 0.1 % acetic acid as eluent. The product containing fractions were combined and the solvent removed at reduced pressure by rotary evaporation to get a pale amber oil, with this product weighing 21.85 g. The oil was dissolved in ether and washed with water and brine to remove acetic acid. The ether layer was then dried over sodium sulfate, filtered and the solvent removed at reduced pressure by rotary evaporation to give 18.6 g of a pale yellow oil. Titration with hexanes gave an off-white solid weighing 14.64 g which was a mixture of the two desired compounds in a 68:32 ratio, as determined by HPLC analysis described in General Methods. No other products were detected by this HPLC analysis.

Example 2

First Step Reaction using Alternative Reagent Addition

A first step reaction was performed with an alternative order of reagent addition, as follows. Into a 250 mL 3-neck jacketed flask equipped with mechanical stirrer and thermometer was added under nitrogen 170.72 g of 1.0 M Hydrobromic acid solution. The solution was cooled to 5° C. using a recirculating chiller. KBr (4.926 g) was added with stirring, resulting in a clear solution. To the solution was added 2.0945 g of $NaNO_2$. Over 30 min while maintaining the temperature at 5° C. was added 5.0 g of tyrosine (Aldrich). The solution turned from a light yellow to orange and gas evolution was observed, with a slight exotherm. The solution was sampled by HPLC as described in General Methods. After 2 h the conversion was found to be 69%, and the yield of product 1 was 39% and of product 2 was 17%.

Example 3

Optimization of Reagent Concentrations in the First Step Reaction

The effects on yield and selectivity of variations in concentration of $NaNO_2$, KBr and HBr in the reaction mixture were tested as follows in a response surface DOE (design of experiments). Into a 250 mL jacketed flask with recirculating cooling fitted with reflux condenser, and nitrogen inlet was added 162 mL of varying concentrations of HBr solution, as listed in Table 3. The HBr solution had been washed with 5% tributylphosphate in chloroform to remove free bromine. Under a nitrogen atmosphere, a varying amount of KBr was added, as listed in Table 3, and the contents of the flask were brought to 5° C. by means of the recirculating chiller. Tyrosine, 5.0 g, was added and the solution stirred to form a clear solution. A varying amount of sodium nitrite, as listed in Table 3, was added portionwise over 30 min so that the temperature did not rise above 10° C. The reaction was allowed to proceed at 5° C. for 120 min. The yield of the two products, shown in Diagram I, was measured using an analytical HPLC method employing a calibration curve for the two desired products, as described in General Methods. Table 3 shows the yield of each product and combined yield of the two products for the different combinations of variables tested (equivalents of $NaNO_2$, equivalents of KBr, concentration of HBr).

TABLE 3

Product formed under different reagent concentrations.

| Example | NaNO2 equiv | HBr(M) | KBr equiv | Yield 1 | Yield 2 | Total yield |
|---|---|---|---|---|---|---|
| 1 | 1 | 0.75 | 0 | 39.415 | 24.36 | 63.775 |
| 2 | 3 | 0.75 | 0 | 27.325 | 24.615 | 51.94 |
| 3 | 1 | 0.75 | 4 | 49.935 | 19.965 | 69.9 |
| 4 | 3 | 0.75 | 4 | 42.405 | 22.42 | 64.825 |
| 5 | 2 | 0.75 | 2 | 48.83 | 26.335 | 75.165 |
| 6 | 1 | 2.375 | 2 | 55.59 | 17.54 | 73.13 |
| 7 | 3 | 2.375 | 2 | 35.6 | 8.65 | 44.25 |
| 8 | 2 | 2.375 | 0 | 35.94 | 19.025 | 54.965 |
| 9 | 2 | 2.375 | 4 | 31.14 | 16.815 | 47.955 |
| 10 | 2 | 2.375 | 2 | 36.35 | 17.875 | 54.225 |
| 11 | 2 | 2.375 | 2 | 41.29 | 19.505 | 60.795 |
| 12 | 2 | 2.375 | 2 | 33.2 | 18.36 | 51.56 |
| 13 | 2 | 2.375 | 2 | 46.48 | 22.05 | 68.53 |
| 14 | 2 | 2.375 | 2 | 42.845 | 19.195 | 62.04 |
| 15 | 1 | 4 | 0 | 22.99 | 8.375 | 31.365 |
| 16 | 3 | 4 | 0 | 2.26 | 5.085 | 7.345 |
| 17 | 1 | 4 | 4 | 20.365 | 6.98 | 27.345 |
| 18 | 3 | 4 | 4 | 4.15 | 4.675 | 8.825 |
| 19 | 2 | 4 | 2 | 16.14 | 9.21 | 25.35 |

Using the data from the Table 3 measuring the total yield of the two brominated products as a function of $NaNO_2$ equivalents, HBr concentration and KBr equivalents a regression was performed to create a reaction model. After eliminating the insignificant cross and square terms, the fitted data using Minitab™ analysis was used to predict optimal conditions based on these three variables. The model predicted an optimal yield of 80% at conditions of 0.75M HBr, 2.03 equivalents of KBr and 1.0 equivalent of $NaNO_2$.

Example 4

Second Step Reaction: Synthesis of p-hydroxystyrene

In the second step reaction the isomeric bromide product mixture of the first step reaction was reacted to form p-hydroxystyrene as shown below:

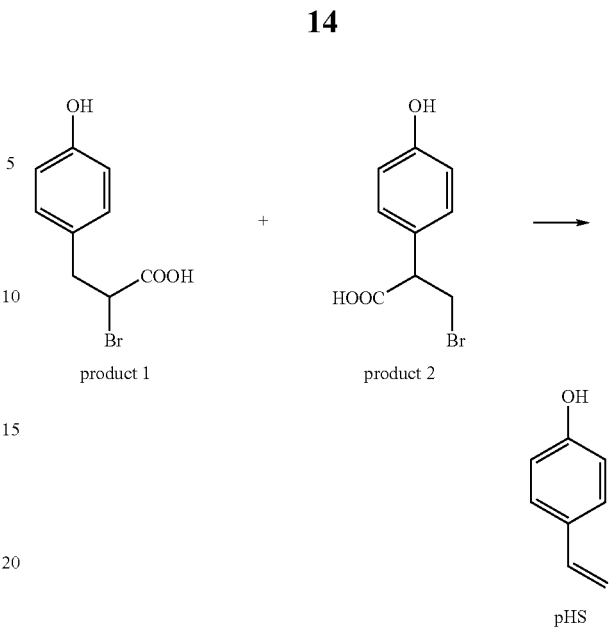

A second step reaction was performed as follows. To a 3-neck 50 mL flask equipped with an overhead stirrer, condenser and nitrogen inlet were added under nitrogen 0.654 g of the purified mixture of isomeric bromides from Example 1 and 4.1 g of potassium carbonate in DMF. The resulting suspension was heated at 60° C. with vigorous stirring for 50 min. Reaction progress was measured by HPLC analysis using a standard curve to quantitate as described in General Methods. The yield of pHS was found to be 50.2%.

Example 5

Synthesis of p-acetoxystyrene

A second step reaction was performed which also included acetylation of pHS, as shown below.

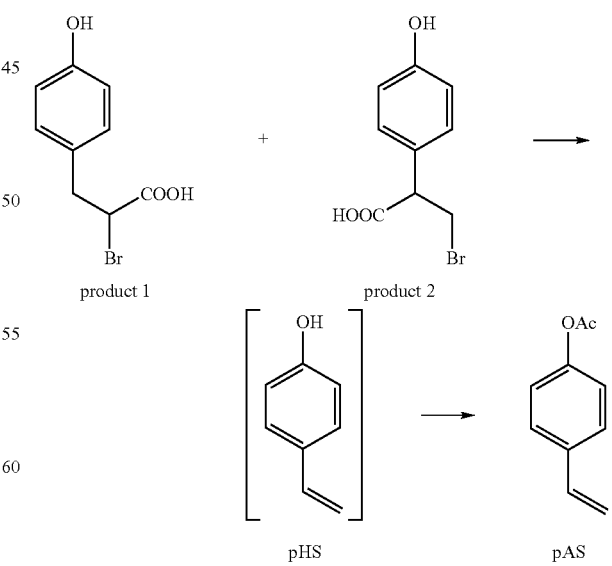

A combined reaction including production of pHS from the isomeric bromide product mixture and acetylation of pHS to produce p-acetoxystyrene was performed as follows. To a 50 mL 3-neck flask equipped with an overhead stirrer, condenser and nitrogen inlet, under nitrogen, were added 1.64 g of the purified mixture of isomeric bromides from Example 1 and 5 mL of DMF. In one portion, 3.04 g of potassium carbonate was added and the mixture heated to 65° C. with stirring. The reaction was monitored by HPLC as described in General Methods. After 1 h, 0.76 mL acetic anhydride was added and heating was continued for 15 min. The reaction mixture was cooled to room temperature, poured into 25 mL of water and extracted 3× with ether. The combined organic extracts were dried over sodium sulfate and the solvent removed at reduced pressure by rotary evaporation to give 0.3 g of the desired product, pAS.

Example 6

Synthesis of p-Hydroxystyrene using Triethylamine as Base

A second step reaction was performed using triethylamine as an alternate base reagent as follows. To a 50 mL 30 neck flask equipped with an overhead stirrer, condenser and nitrogen inlet, under nitrogen, was added 0.167 g of the purified mixture of isomeric bromides from Example 1 and 1.8 mL DMF. After adding 0.67 g of triethylamine, the reaction mixture was heated to 60° C. and the reaction was followed by HPLC, as described in General Methods. The yield of pHS—after 20 h was found to be 28%.

Example 7

Synthesis of p-Hydroxystrene using Potassium Acetate as Base

A second step reaction was performed using potassium acetate as an alternate base reagent as follows. To a 50 mL 3-neck flask equipped with a mechanical stirrer, condenser, and nitrogen inlet, was added under nitrogen 1.271 g of the purified mixture of bromides from Example 1 and 6.797 g of DMF. To the resulting solution was added 0.447 g of KOAc and the reaction mixture was raised to 65° C. The reaction mixture was stirred for 1.3 h and then the temperature was raised to 80° C. After 40 min at 80° C., the temperature was again raised to 135° C. and left for 1 h with stirring. The reaction was continuously monitored by HPLC, as described in General Methods. The yield of p-hydroxystyrene was 3%.

Example 8

Synthesis of p-Hydroxystrene using Sodium Bicarbonate as Base

A second step reaction was performed using sodium bicarbonate as an alternate base reagent as follows. To a 25 mL round bottom flask equipped with a condesnor, nitrogen inlet and magnetic stirring was added under nitrogen 0.3052 g of the purified mixture of the isomeric bromides from Example 1 and 1.88 g DMF. Sodium bicarbonate (0.305 g) as added in one portion and the reaction was stirred at 60° C. for 2.75 h. HPLC showed a yield of 12% for pHS.

Example 9

Diazochlorination of Tyrosine—Comparative Example

Tyrosine was diazochlorinated, providing a comparison to the diazobromination of tyrosine in Examples 1-3. Into a 100 mL 3-neck flask fitted with thermometer adaptor was added 5.0 g tyrosine and 24 mL 6N HCl. The resulting suspension was brought to 0° C. with a dry ice acetone bath. To the mixture was added 2.02 g sodium nitrite over 35 min and the mixture was then stirred an additional 2 h at 0-5° C. The brown solution was warmed to room temperature and extracted 3× with 10 mL of ether. The extracts were dried over sodium sulfate and the ether was removed to give 2.55 g of a yellow oil. NMR showed the oil to be a mixture of the desired product, which is the same as products 1 and 2 in Example 1 except that Cl is substituted for Br, and a product that had been nitrated ortho to the phenolic group. The mixture was separated using preparative HPLC and the products identified by HPLC MS and $^1$H NMR. The nitration products were found to amount to about 40 mol % of theoretical yield. The presence of the ortho nitrated product in the diazochlorination reaction products prevents the direct use of the product mixture as a reagent in a second reaction to produce p-hydroxystyrene, unlike the diazobromination reaction of Examples 1-3. Separation of the nitrated products was difficult, requiring repeated recrystalizations and or chromatography steps. The nitration on the ring also makes the product mixture unusable for elaboration to the styrene, especially for uses such as photoresists where the UV absorption by the nitroaryl group would be detrimental.

Example 10

Separation of 2-Bromo-3-(p-hydroxyphenyl)propionic acid from 3-Bromo-2-(p-hydroxyphenyl)propionic acid2-Bromo-3-(p-hydroxyphenyl)propionic acid and 3-Bromo-2-(p-hydroxyphenyl)propionic acid in an isomeric bromide product mixture were individually isolated using reverse phase chromatography on a preparative HPLC using a 150× 22 mm C-18A 10 µ column from Metachem Technologies (Palo Alto, Calif.). The mobile phase was: Solvent A: Water/ 0.1% Trifluoroacetic acid and Solvent B: Acetonitrile/0.1% trifluoroacetic acid with a flow rate of 20 mL/min. The gradient in the following table was used with peak detection at 220 and 254 nm. 3-Bromo-2-(p-hydroxyphenyl)propionic acid was the first component to elute with retention time 11.5 min followed by 2-bromo-3-(p-hydroxyphenyl)propionic acid at 15 min. Product containing fractions were combined and evaporated to dryness.

TABLE 4

| Solvent Gradient for preparative HPLC method. | |
|---|---|
| Time (min) | % B |
| 0.00 | 5 |
| 29.5 | 100 |
| 36.5 | 100 |
| 43.0 | 5 |

What is claimed is:
1. A method for the synthesis of p-hydroxystyrene comprising:
 a) reacting tyrosine in the presence of HBr and NaNO2 to form an isomeric bromide product mixture of 2-bromo-

(3-p-hydroxyphenyl) propionic acid and 3-bromo-(2-p-hydroxyphenyl) propionic acid, according to Formula I:

Formula I:

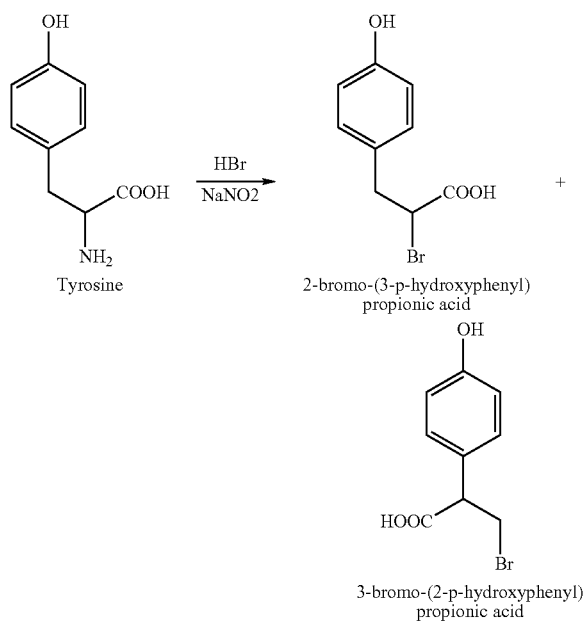

b) isolating the isomeric bromide product mixture of (a); and c) reacting the isolated isomeric bromide product mixture of b) with a basic catalyst in an organic solvent wherein p-hydroxystrene is produced according to Formula II Formula II:

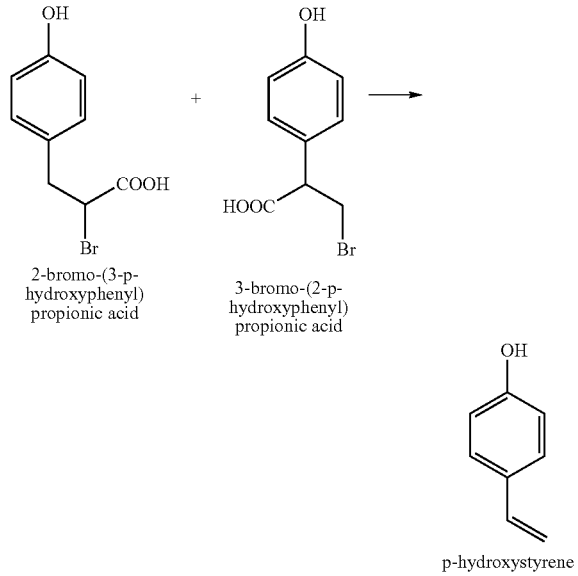

2. The method of claim 1 wherein the reaction of step (a) occurs at a temperature between about −10° C. and about 25° C.

3. The method of claim 1 wherein the temperature of (c) is between about −5° C. and about 10° C.

4. The method of claim 1 wherein step (a) optionally comprises a bromide salt.

5. The method of claim 4 wherein the bromide salt is selected from the group consisting of NaBr and KBr.

6. The method of claim 1 wherein the organic solvent is selected from the group consisting of (i) an aprotic, polar organic solvent; (ii) a protic, polar organic solvent; and (iii) mixtures thereof.

7. The method of claim 6 wherein the protic, polar organic solvent is selected from the group consisting of di(propylene glycol) methyl ether (Dowanol™ DPM), di(ethylene glycol) methyl ether, 2-butoxyethanol, ethylene glycol, 2-methoxyethanol, propylene glycol methyl ether, n-hexanol, and n-butanol.

8. The method of claim 6 wherein the aprotic, polar organic solvent is selected from the group consisting of N,N-dimethylformamide, 1-methyl-2-pyrrolidinone, N,N-dimethylacetamide, dimethylsulfoxide, hexamethylphosphoramide, and hexamethylphosphorous triamide.

9. The method of claim 1 wherein the basic catalyst is selected from the group consisting of potassium acetate, potassium carbonate, potassium hydroxide, sodium acetate, sodium carbonate, sodium bicarbonate, sodium hydroxide, magnesium oxide, pyridine, and triethylamine.

10. The method of claim 1 wherein step (b) optionally comprises a polymerization inhibitor.

11. A method of claim 10 wherein the polymerization inhibitor is selected from the group consisting of hydroquinone, hydroquinone monomethylether, 4-tert-butyl catechol, phenothiazine, N-oxyl (nitroxide) inhibitors, 4-hydroxy-TEMPO (4-hydroxy-2,2,6,6-tetramethylpiperidin-1-yloxy, CAS#2226-96-2) and Uvinul® 4040 P (1,6-hexamethylene-bis(N-formyl-N-(1-oxyl-2,2,6,6-tetramethylpiperidine-4-yl)amine).

12. The method of claim 1 wherein step (b) optionally comprises a polymerization retarder.

13. The method of claim 12 wherein the polymerization retarder is selected from the group consisting of dinitroortho-cresol (DNOC) and dinitrobutylphenol (DNBP).

14. A method for the synthesis of p-acetoxystyrene comprising:

a) reacting tyrosine in the presence of HBr and NaNO2 to form an isomeric bromide product mixture of 2-bromo-(3-p-hydroxyphenyl) propionic acid and 3-bromo-(2-p-hydroxyphenyl) propionic acid, according to Formula I:

Formula I:

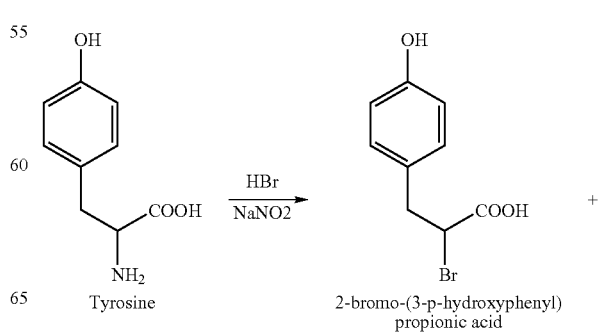

-continued

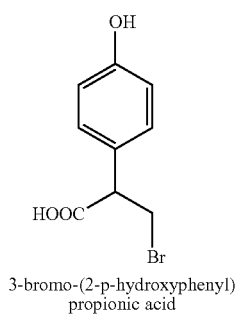

3-bromo-(2-p-hydroxyphenyl) propionic acid b) isolating the isomeric bromide product mixture of (a); and c) reacting the isolated isomeric bromide product mixture of b) with a basic catalyst in an organic solvent wherein p-hydroxystrene is produced according to Formula II Formula II:

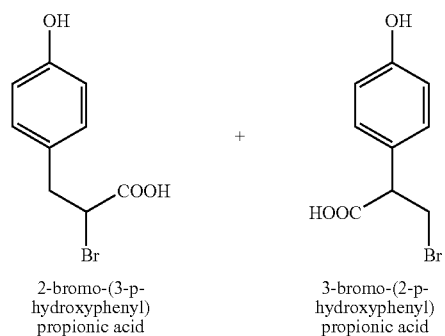

2-bromo-(3-p-hydroxyphenyl) propionic acid 3-bromo-(2-p-hydroxyphenyl) propionic acid -continued

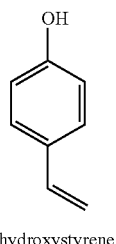

p-hydroxystyrene and d) reacting the p-hydroxystyrene of step (c) with an acetylating agent wherein p-acetoxystyrene is formed.

15. The method of claim 14 wherein the p-hydroxystyrene is first isolated prior to the reaction step (d) with an acetylating agent.

16. The method of claim 14 wherein the p-hydroxystyrene is not isolated prior to the reaction step (d) with an acetylating agent.

17. The method of claim 14 wherein the acetylating agent is selected from the group consisting of acetic anhydride and acetyl chloride.

18. The method of claim 14 wherein the reaction of step (a) occurs at a temperature between about −10° C. and about 25° C.

19. The method of claim 14 wherein step (a) optionally comprises a bromide salt.

20. The method of claim 15 wherein the organic solvent is selected from the group consisting of (i) an aprotic, polar organic solvent; (ii) a protic, polar organic solvent; and (iii) mixtures thereof.

21. The method of claim 16 wherein the solvent is an aprotic, polar organic solvent.

22. The method of claim 14 wherein step (b) optionally comprises a polymerization inhibitor.

23. The method of claim 14 wherein Step (b) optionally comprises a polymerization retarder.

* * * * *